(12) United States Patent
Herzberg et al.

(10) Patent No.: US 6,309,368 B1
(45) Date of Patent: Oct. 30, 2001

(54) KNEE-JOINT ORTHESIS (75) Inventors: Thorsten Herzberg, Hamburg; Andreas Albrod, Seevetal, both of (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/125,135
(22) PCT Filed: Jan. 21, 1997
(86) PCT No.: PCT/EP97/00264
   § 371 Date: Aug. 12, 1998
   § 102(e) Date: Aug. 12, 1998
(87) PCT Pub. No.: WO97/29718
   PCT Pub. Date: Aug. 21, 1997

(30) Foreign Application Priority Data

Feb. 16, 1996 (DE) .............................. 196 05 734

(51) Int. Cl.$^7$ ...................................... A61F 5/00
(52) U.S. Cl. .................... 602/26; 602/5; 602/16
(58) Field of Search .................. 602/16, 23, 26

(56) References Cited

U.S. PATENT DOCUMENTS

| | | | | |
|---|---|---|---|---|
| 4,681,097 | * | 7/1987 | Pansiera | 128/77 |
| 4,966,133 | * | 10/1990 | Kausek | 128/80 C |
| 5,292,303 | * | 3/1994 | Bastyr et al. | 602/16 |
| 5,330,418 | * | 7/1994 | Townsend et al. | 602/26 |
| 5,676,640 | * | 10/1997 | Biederman | 602/26 |
| 5,938,629 | * | 8/1999 | Bloedau | 602/16 |

* cited by examiner

*Primary Examiner*—Kim M. Lewis
(74) *Attorney, Agent, or Firm*—Norris McLaughlin & Marcus (57) ABSTRACT

Knee-joint orthesis with a lower leg part and a thigh part, and with a lateral orthesis hinge and a medial orthesis hinge which connect the lower leg part and the thigh part to each other, characterized in that the lateral orthesis hinge is formed by a hinge which consists of two intermeshing toothed wheels whose axles are each securely connected on both sides to a hinge plate, each of the two toothed wheels having in each case a strut which is used for securely connecting the lateral orthesis hinge to the lower leg part and to the thigh part, the medial orthesis hinge is formed by a single-axle hinge which consists of a U-shaped upper part which encloses a lower part, the upper part and lower part being connected to each other in an articulated manner by means of a pin.

8 Claims, 9 Drawing Sheets

KNEE-JOINT ORTHESIS

The invention relates to a knee-joint orthesis which has two different orthesis hinges so that a displacement of the pivot axis of the knee-joint orthesis is possible upon movement and extension.

From work carried out on the biomechanics of the knee joint, it has been scientifically demonstrated that the human knee joint is subject to a multi-dimensional movement. Flexion and extension of the joint take place about a pivot axis which is not fixed in location and which thus changes its position. This results from the relative position of the anterior and posterior cruciate ligaments. Scientific investigations have shown that the pivot point is displaced by about 14 mm in the dorsal direction and by about 3 mm in the caudal direction on the outer side of the joint during flexion. The change in position of the pivot axis on the inner side of the joint is negligibly small. The result of this is an outward pivoting of the lower leg during flexion.

In order to protect the damaged and, where appropriate, surgically reconstructed knee joint, so-called functional orthesis are used nowadays. The basic principle of their construction is a solid frame consisting of a thigh part and of a lower leg part. The two parts of this orthesis are connected to one another by a hinge on the medial side and on the lateral side.

In the case of the products already known in the prior art, the hinges are of identical construction on both sides, whether single-axle or polycentric. This results without exception in a mechanism which is subject to one pivot axis. Some constructions displace the pivot axis symmetrically towards the rear, i.e. the pivot point migrates rearwards to the same extent on the outer side and inner side. The lower leg rotation, which is necessary from biomechanical considerations, is not permitted.

The object of the invention is to make available a knee-joint orthesis which, like the human knee joint, is able to permit the displacement of the pivot axis upon movement and extension of the joint.

This object is achieved by the knee-joint orthesis having a lower leg part and a thigh part, and having lateral orthesis hinge and a medial orthesis hinge which connect the lower leg part and the thigh part to each other, characterized in that the lateral orthesis hinge is formed by a hinge which consists of two intermeshing toothed wheels whose axles are each securely connected on both sides to a hinge plate, each of the two toothed wheels having in each case a strut which is used for securely connecting the lateral orthesis hinge to the lower leg part and to the thigh part, the medial orthesis hinge being formed by a single-axle hinge which consists of a U-shaped upper part which encloses a lower part, the upper part and lower part being connected to each other in an articulated manner by means of a pin.

The knee-joint orthesis according to the invention consists of a lower leg part and of a thigh part which are fixed to the respective leg section. The connection of the lower leg part and of the thigh part is effected by a lateral orthesis hinge and a medial orthesis hinge.

The lateral orthesis hinge is formed by a hinge which consists of two intermeshing toothed wheels whose axles are each securely connected on both sides to a hinge plate. Each of the two toothed wheels has a strut which ensures the connection of the lateral orthesis hinge to the lower leg part and to the thigh part.

The medial orthesis hinge is formed by a single-axle hinge which is composed of a U-shaped upper part and of a lower part enclosed by the upper part, where the upper part and lower part are connected to one another in an articulated manner by a pin. Advantageously, the pin has a slight spherical shape in the hinge-forming section.

The connection of the lower leg part and of the thigh part to the lateral orthesis hinge and the medial orthesis hinge is preferably effected using an adjustment device.

To form the adjustment device, the upper strut and the lower strut of the lateral orthesis hinge, the upper part and the lower part of the medial orthesis hinge and the distal section of the thigh part in the lateral side and in the medial side, and the proximal section of the lower leg part in the lateral side and in the medial side, in each case have an oblong slot. The oblong slots in the thigh part and in the lower leg part are in each case offset in particular by 90° in relation to the oblong slots in the struts of the lateral orthesis hinge and in the upper part and in the lower part of the medial orthesis hinge. The two corresponding oblong slots are in each case connected centrally via a slide bracket, movement of the respective parts being prevented with the aid of a central locking screw.

The upper of the two toothed wheels in the lateral orthesis hinge preferably has a smaller radius than the lower one, the upper one preferably having a radius of 15 mm and the lower one preferably having a radius of 27 mm.

This permits the advantageous displacement of the pivot point of the lateral orthesis hinge during the movement of the knee-joint orthesis from 0° extension to 90° flexion, by about 14 mm in the dorsal direction and 3 mm in the caudal direction.

Stop means are advantageously provided on the lateral orthesis hinge and on the medial orthesis hinge in order to limit the extension and flexion of the knee-joint orthesis.

In the lateral orthesis hinge, the device for limiting the extension and flexion preferably consists of an oblong slot in the form of a portion of a circle in the lower toothed wheel, of oblong slots, likewise in the form of a portion of a circle, on the medial hinge plate and on the lateral hinge plate, the three oblong slots being congruent when the knee-joint orthesis is extended. The oblong slots on the hinge plates preferably have a slightly narrower width than the oblong slot in the lower toothed wheel.

In addition, use is made of two sleeves which extend from the medial hinge plate into the oblong slot of the lateral hinge plate. Screws are guided in the inside of the sleeves, which screws are secured by means of nuts which are guided in the oblong slot of the medial hinge plate and are thus secured against rotation. And fix the sleeves in their position in the oblong slot on the lateral hinge plate.

The thigh part and the lower leg part of the knee-joint orthesis preferably consist of a frame structure which is applied in particular to the anterior aspect of the leg. This frame structure is made up, preferably in composite design, from a combination of an individually shapeable light metal frame with corresponding inner pads and of an outer frame covering.

The knee-joint orthesis according to the invention affords a number of advantages, which demand that this orthesis be used when it is necessary to immobilize the knee or in the event of post-operative rehabilitation of the knee.

Thus, by using two differently designed orthesis hinges, of which the lateral orthesis hinge is a toothed wheel joint, it is possible to displace the pivot axis of the knee-joint orthesis, as is necessary according to the most recent scientific knowledge, so as not to adversely effect the natural pattern of movement of the knee joint.

Furthermore, because of the special design of the lateral orthesis hinge, the necessary limitation of the extension and flexion of the knee-joint orthesis is particularly easy to set.

The advantageous design of the medial orthesis hinge as a type of ball joint permits the three-dimensional movement of the medial orthesis hinge, thus ruling out the possibility of the latter becoming jammed as the pivot axis migrates during the course of a movement. This orthesis hinge also makes it possible in a particularly simple manner to limit the extension and flexion of the knee-joint orthesis.

The special adjustment device which serves to connect the two orthesis hinges to the thigh part and to the lower leg part makes it possible to bring the knee-joint orthesis individually to the anatomically optimum position and at the same time to reduce to a minimum any micro-movements in relation to the knee joint. In addition, this adjustment device can be used for varus or valgus correction.

The frame structure of the thigh part and of the lower leg part, in composite design, in a combination of an individually shapeable light metal frame with corresponding inner pads and of an outer frame covering, protects the knee joint particularly advantageously from external knocks and jolts, while at the same time, however, the anterior placement on the leg does not prevent a complete bending of the knee joint.

In addition, the frame structure affords the advantage of protecting clothing from mechanical influences.

An illustrative embodiment is shown in the drawings, in which.

Figure 1:
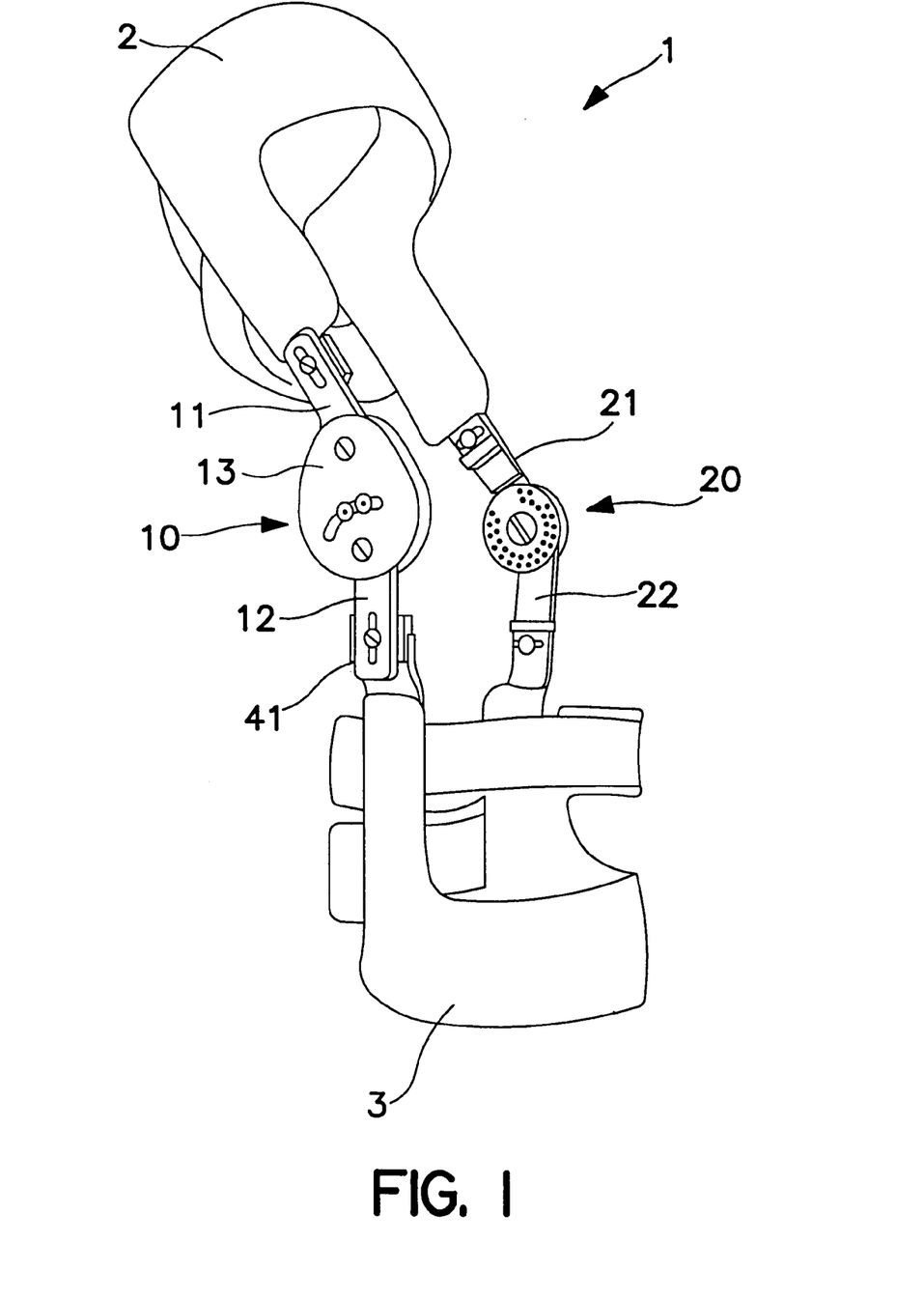
FIG. 1 shows the knee-joint orthesis for the right leg, viewed from the lateral side.

FIG. 1 shows a particularly advantageous embodiment of the knee-joint orthesis (1), namely a knee-joint orthesis (1) for the right leg. The knee-joint orthesis (1) consists of a thigh part (2), a lower leg part (3), a lateral orthesis hinge (10), consisting of an upper toothed wheel (11), a lower toothed wheel (12) and a lateral hinge plate (13), and also a medial orthesis hinge (20), consisting of an upper part (21) and of a lower part (22) which are connected to each other in an articulated manner. The connection of thigh part (2) and lower leg part (3) to the, two orthesis hinges (10, 20) is in each case effected via a so-called fastening means, the main component of which is in each case a slide bracket (41).

Figure 2:
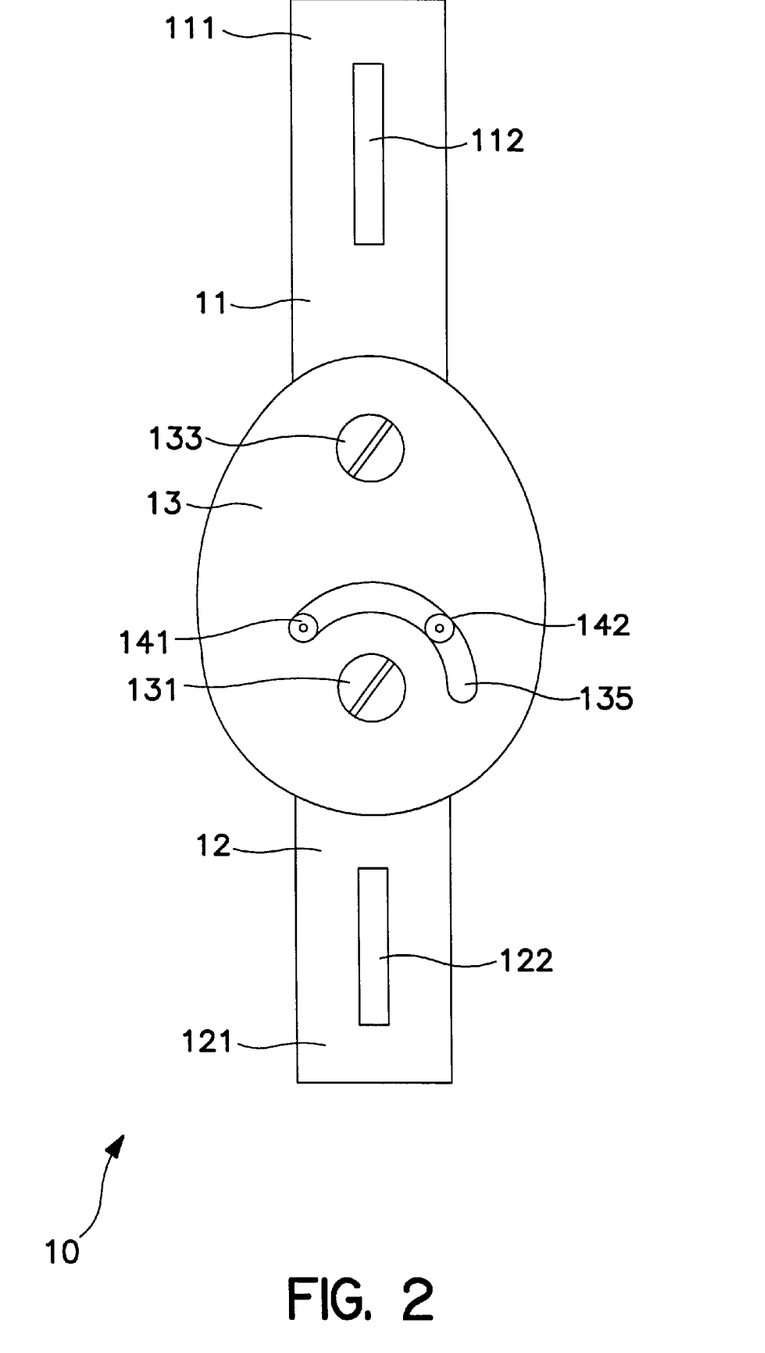
FIG. 2 shows the lateral orthesis hinge, specifically the lateral side.

According to FIG. 2, the lateral orthesis hinge (10) is formed by the upper toothed wheel (11) and by the lower toothed wheel (12). For connecting them, use is made of the lateral hinge plate (13), which fixes the toothed wheels (11, 12) by means of screws (131, 133). Both the strut (111) of the upper toothed wheel (11) and the strut (121) of the lower toothed wheel (12) have an oblong slot (112, 122) used for connecting to the thigh part (2) and to the lower leg part (3), respectively, of the knee-joint orthesis (1). The lateral hinge plate (13) is preferably of elliptic configuration in order to safely cover the toothed rings of the toothed wheels (11, 12).

Furthermore, the lateral hinge plate (13) has an oblong slot (135) in the form of a portion of a circle, the purpose of which is to limit the maximum extension and flexion by the two fixed sleeves (141, 142).

Figure 3:
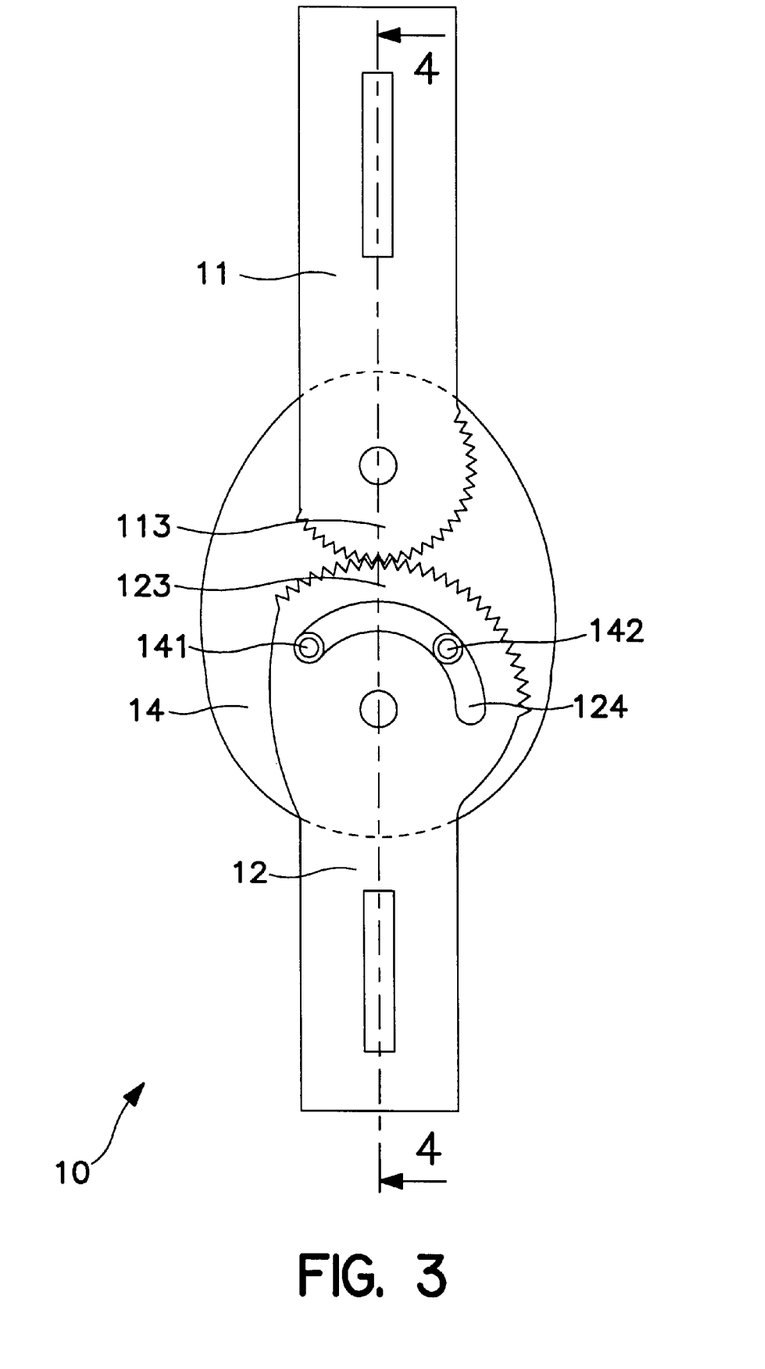
FIG. 3 shows the lateral orthesis hinge without the lateral joint plate.

FIG. 3 shows the lateral orthesis hinge (10) after removal of the lateral hinge plate (13). The two toothed wheels (11, 12) are connected fixedly to the medial hinge plate (14), which preferably has the same dimensions as the lateral hinge plate (13). The toothed rims (113, 123) of the two toothed wheels (11, 12) mesh with one another near the centre of gravity of the surface of the medial hinge plate (14).

The lower toothed wheel (12) has a means for limiting the maximum extension and flexion of the lateral orthesis hinge (10). The said means consists of an oblong slot (124) in the form of a circular cutout in the lower toothed wheel (12), an oblong slot on the medial hinge plate (14) in the form of a portion of a circle which is congruent with the oblong slot (124) when the orthesis hinge (10) is extended, the likewise congruent oblong slot (135) on the lateral hinge plate (13), and two sleeves (141, 142) which can be fixed by means of screws and nuts and extend into the oblong slot (135) in the lateral hinge plate (13). The anterior sleeve (141) here limits the extension of the lateral orthesis hinge (10), and the posteriorly situated sleeve (142) limits the flexion.

Figure 4:
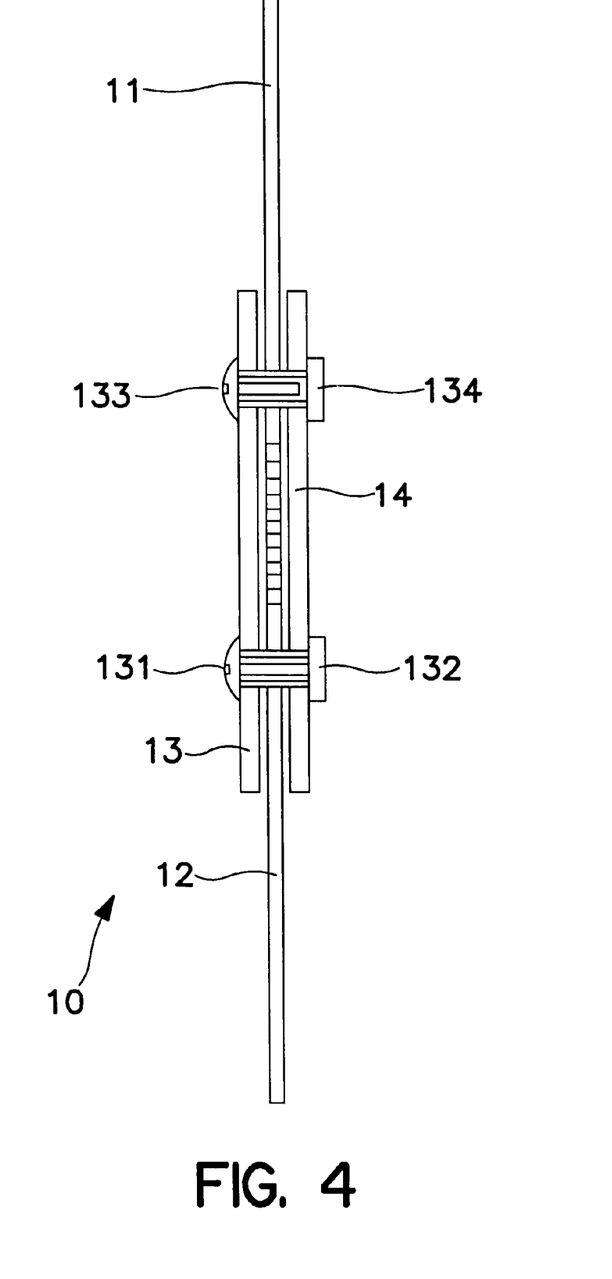
FIG. 4 shows the lateral orthesis hinge in vertical section according to line 4—4 in FIG. 3.

FIG. 4 shows the lateral orthesis hinge (10) in a vertical section according to line 4—4 in FIG. 3. Two screws (131, 133) fix the lateral hinge plate (13), the medial hinge plate (14) lying congruent to the latter (13), and the upper toothed wheel (11) and the lower toothed wheel (12). The screws (131, 133) are locked by two nuts (132, 134).

Figure 5:
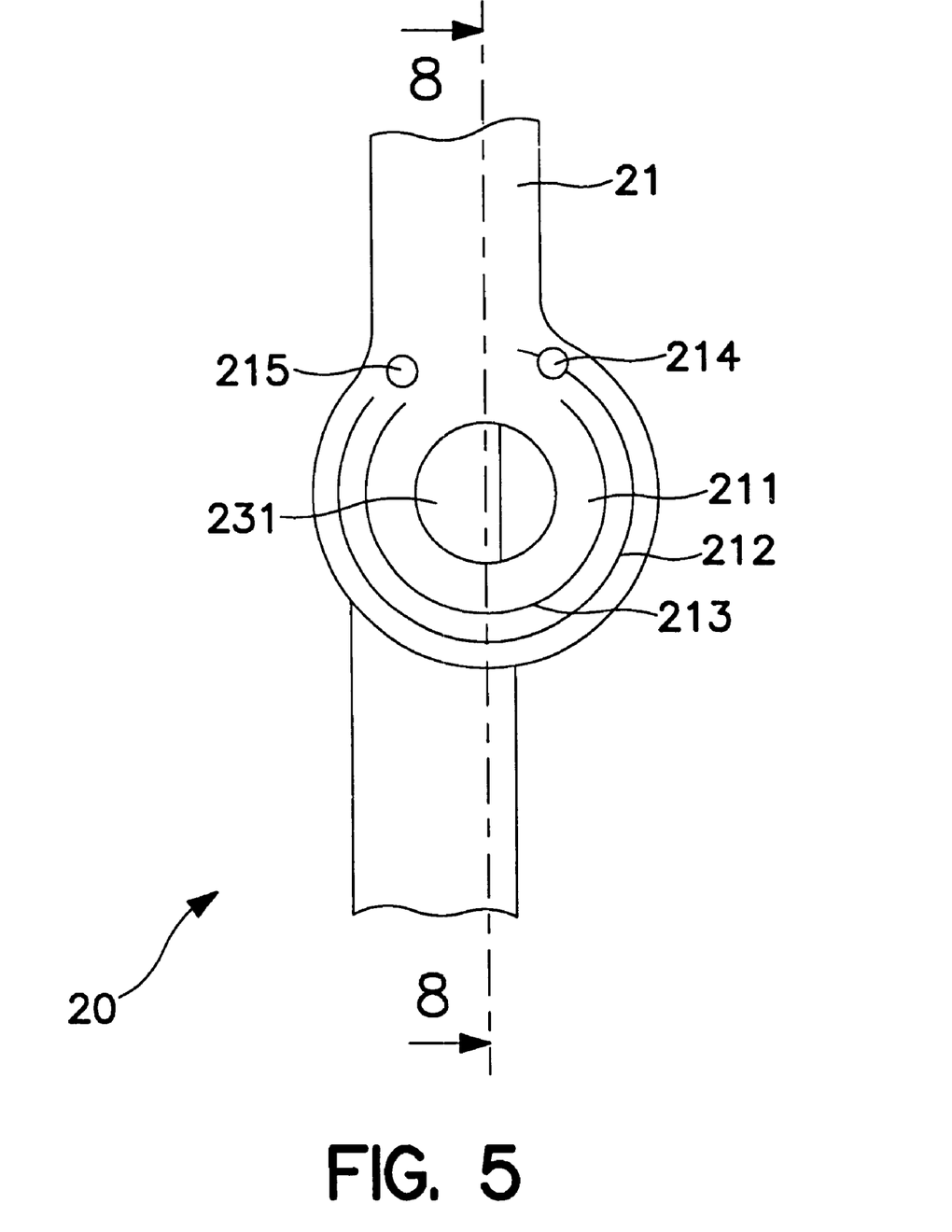
FIG. 5 shows the medial orthesis hinge, specifically the lateral side.

FIG. 5 shows the medial orthesis hinge (20) from the lateral side. The upper part (21) has a preferably circular lateral end section (211). Provided on this end section (211) there are two concentric circles (212, 213) of equidistant bores, the centre point representing the hinge axis of the medial orthesis hinge (20). With the aid of two locking screws (214, 215), the extension and flexion of the medial orthesis hinge (20) can be limited.

A screw (231) situated in the hinge axis secures the connection of upper part (21) and lower part (22).

Figure 6:
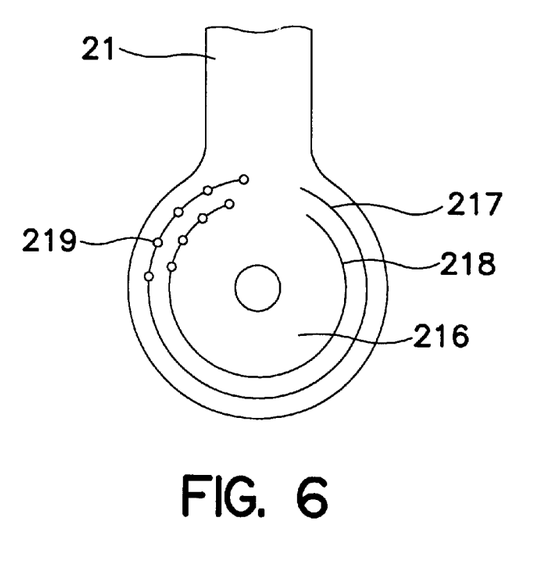
FIG. 6 shows the upper part of the medial orthesis hinge from the medial direction.

FIG. 6 shows the upper part (21) of the medial orthesis hinge (20), specifically from the medial side. On the medial end section (216), which is once again circular, there are two concentric circles (217, 218) of equidistant threaded bores (219). These circles (217, 218) are congruent with the circles (212, 213) on the lateral end section (211). Thus, in cooperation with the locking screws (214, 215), the extension and flexion of the medial orthesis hinge (20) can be limited in preferably 10° stages.

Figure 7:
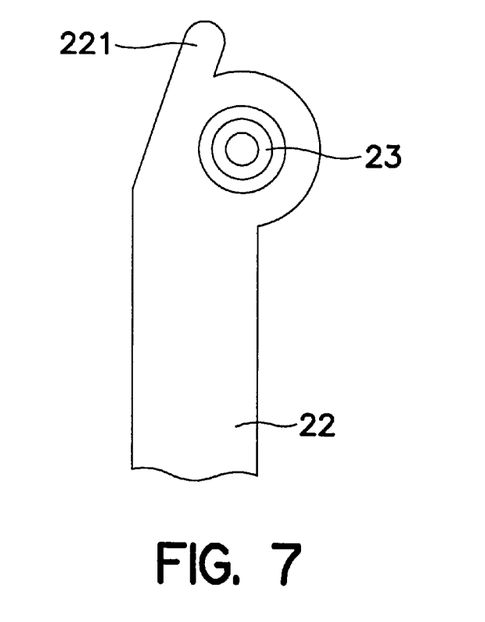
FIG. 7 shows the lower part of the medial orthesis hinge.

As is shown in FIG. 7, the pin (23), preferably having a slight spherical shape, is pressed in securely with the lower part (22). The nose (221) lies between the locking screws (214, 215) and in this way limits the possible movement of the medial orthesis hinge (20).

Figure 8:
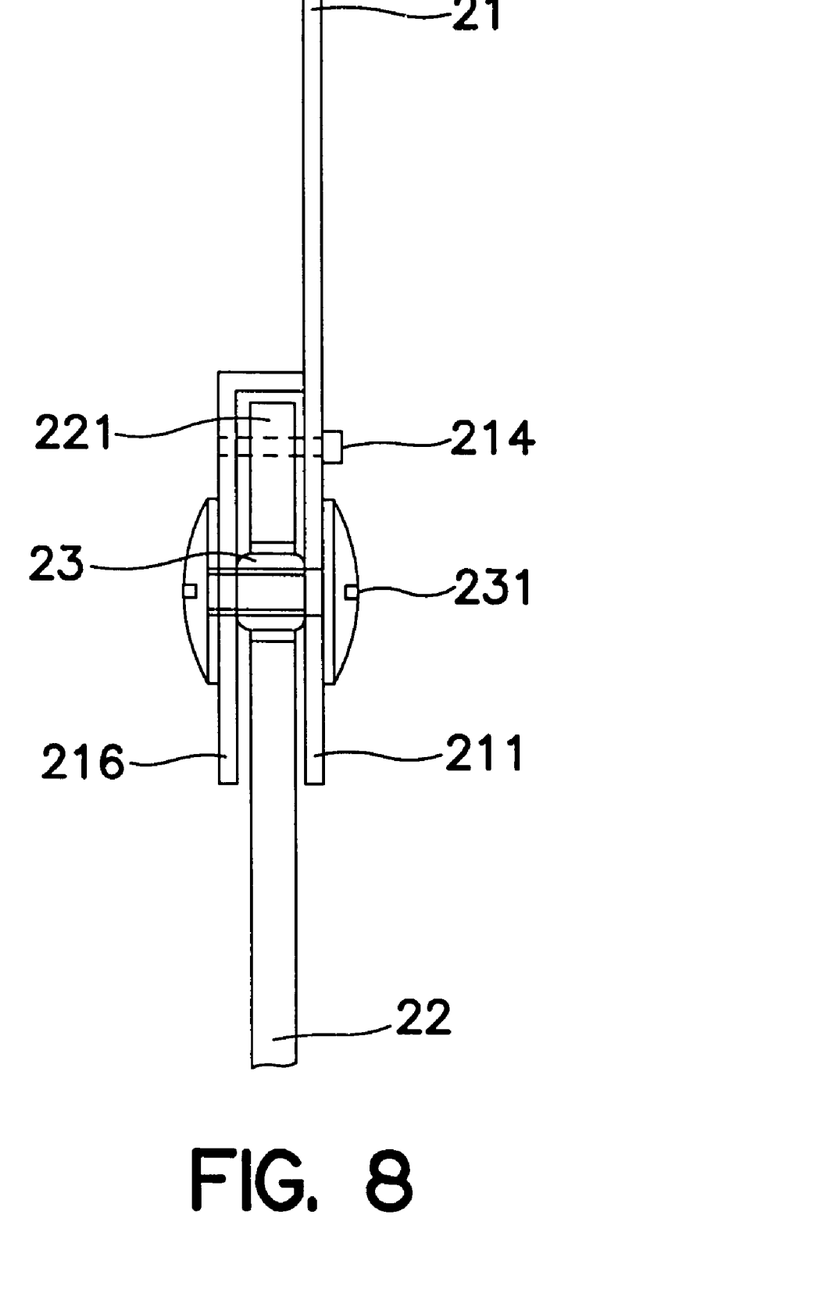
FIG. 8 shows the medial orthesis hinge in vertical section according to line 8—8 in FIG. 5.

FIG. 8 shows the medial orthesis hinge in vertical section according to line 8—8 in FIG. 5, the U-shaped upper part (21) encloses the lower part (22) via the two preferably circular end sections (211, 216). Situated in the hinge axis is the screw (231) which, passing through the pin (23), ensures the secure connection of upper part (21) and lower part (22). The nose (221) provided on the lower part (22) extends into the area of the upper part (21) in which the locking screws (214, 215) are arranged.

Figure 9:
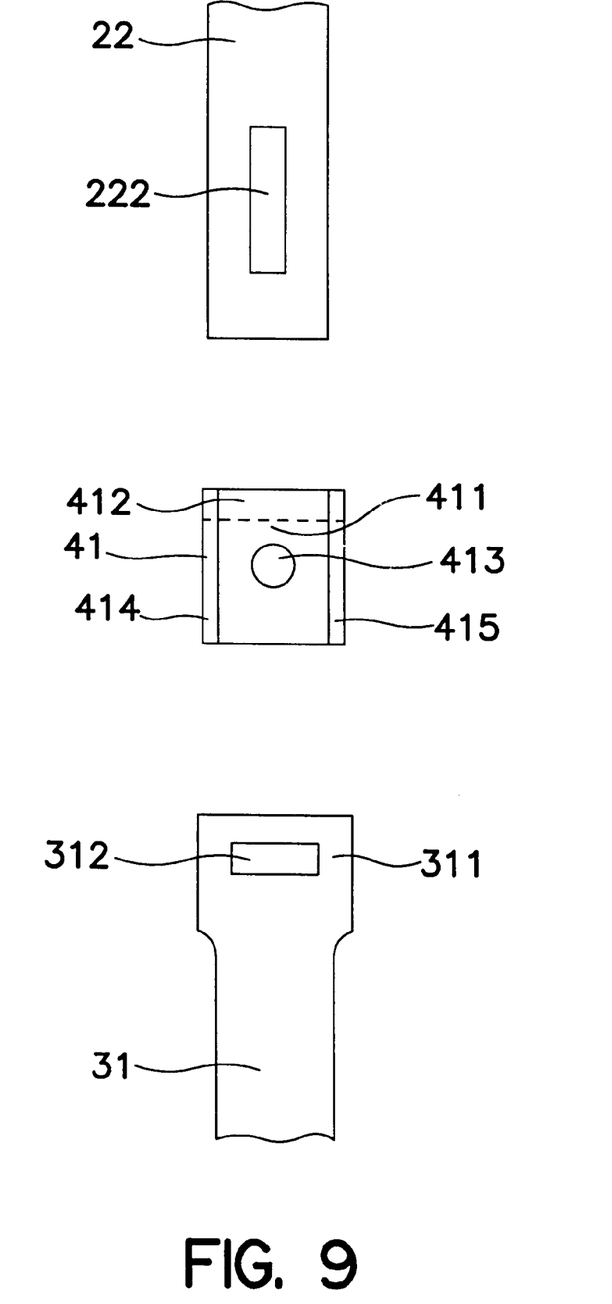
FIG. 9 shows the individual components of the fastening means of the adjustment device.
Figure 10:
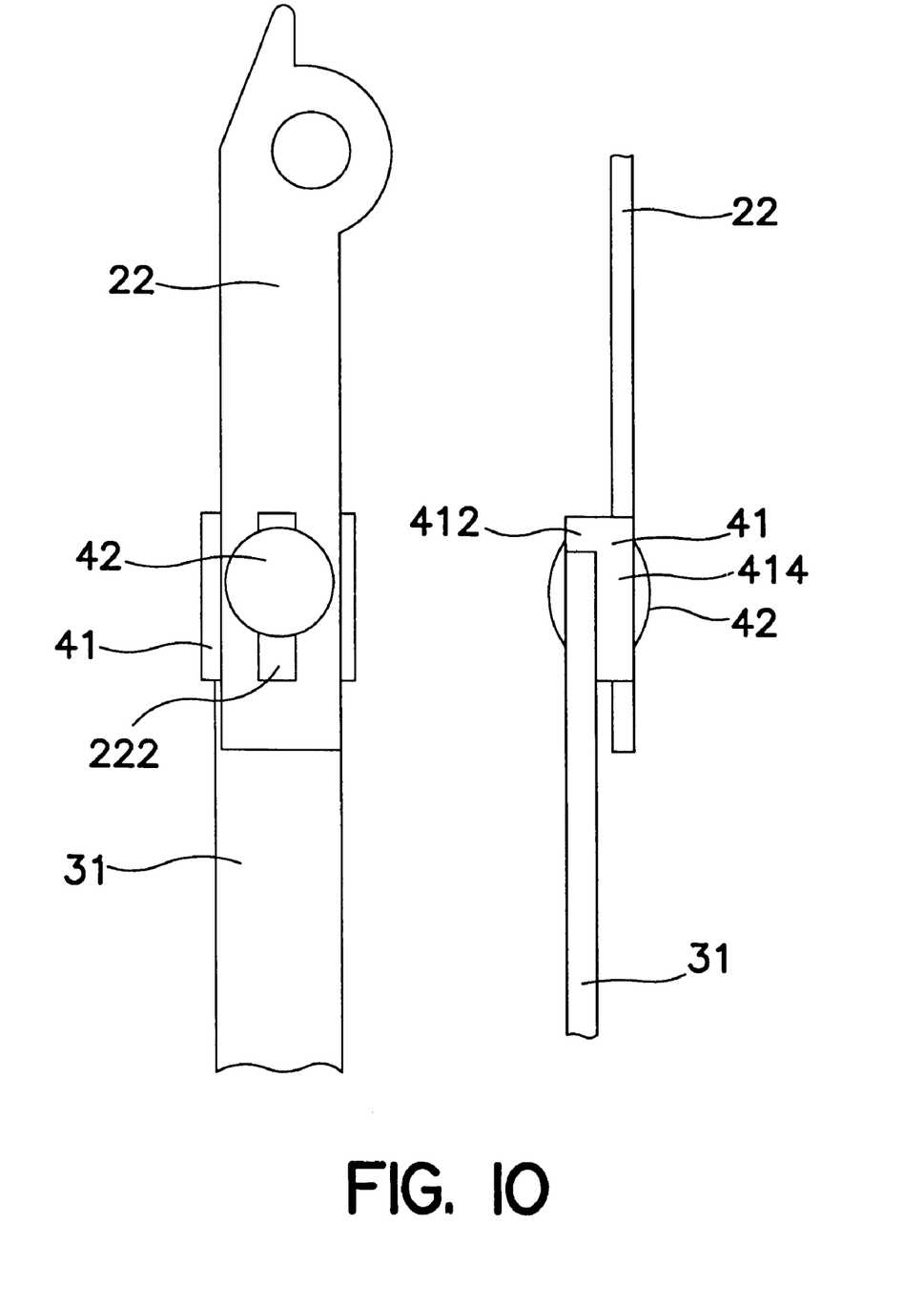
FIG. 10 shows the fastening means of the adjustment device, specifically from the lateral and anterior directions.

As examples of the four fastening means present for the adjusting device of the knee-joint orthesis (1), FIGS. 9 and 10 show the fastening means which ensures the connection of the lower part (22) of the medial orthesis hinge (20) to the lower leg part (31) of the knee-joint orthesis, specifically from the lateral direction and from the anterior direction, in the assembled state and with the components separate. According to FIG. 9, the fastening means consists of lower part (22), slide bracket (41) and proximal section of the lower leg part (31). An oblong slot (222) is provided in the distal direction in the lower part (22). Accordingly, the proximal section of the lower leg part (31) has, at its rectangular end piece (311), an oblong slot (312) in the anterior direction.

The connection of the two oblong slots (222, 312) thus offset by 90° is effected by a slide bracket (41). The slide bracket (41) has, in the medial direction, a U-shaped recess (411) which is used to receive the lower part (22) and which thus, via the lateral edges (414, 415), rules out movement of the lower part (22) to the anterior or posterior direction. Moreover, the slide bracket (41) has at its centre a bore (413) which corresponds to the oblong slots (222, 312). In order to prevent a movement of the proximal section of the lower leg part (31) in the proximal direction, the slide bracket (41) has a stop edge (412) extending across its entire width.

FIG. 10 shows the fastening means in the assembled state. The oblong slots (222, 312) make it possible, in conjunction with the slide bracket (41), to adapt the fastening means individually to the particular dimensions of the knee and in this fastening means [lacuna] lower leg of the wearer of the knee joint orthesis (1) The locking is effected by means of a screw (42).

Accordingly, fastening means are also provided at the other three linkage points between the orthesis hinges (10, 20) and the thigh part (2) and the lower leg part (3), which fastening means permit an optimum adaptation of the knee-joint orthesis (1) to the physical conditions of the particular wearer's knee.

What is claimed is:

1. Knee-joint orthesis comprising a lower leg part and a thigh part, and with a lateral orthesis hinge and a medial orthesis hinge which connect the lower leg part and the thigh part to each other, wherein the lateral orthesis hinge is formed by a hinge which consists of two intermeshing toothed wheels whose axles are each securely connected on both sides to a hinge plate, each of the two toothed wheels having in each case a strut which is used for securely connecting the lateral orthesis hinge to the lower leg part and to the thigh part, the medial orthesis hinge is formed by a single-axle hinge which consists of a U-shaped upper part which encloses a lower part, a lower part having a ball joint enclosed by the U-shaped upper part, the upper part and lower part being connected to each other in an articulated manner by means of a screw passing through the U-shaped upper part and the ball of the ball joint of the lower part.

2. Knee-joint orthesis according to claim 1, wherein that the upper of the two toothed wheels in the lateral orthesis hinge has a smaller radius than the lower one, the upper one preferably having a radius of 15 mm and the lower one preferably having a radius of 27 mm.

3. Knee-joint orthesis according to claim 1, wherein the pivot point of the lateral orthesis hinge, during the movement of the knee-joint orthesis from 0° extension to 90° flexion, is displaced by about 14 mm in the dorsal direction and 3 mm in the caudal direction.

4. Knee-joint orthesis according to claim 1, wherein the extension and flexion of the lateral orthesis hinge and of the medial orthesis hinge can be limited by stop means.

5. Knee-joint orthesis according to claim 1, wherein the device for limiting the extension and flexion on the lateral orthesis hinge consists of an oblong slot in the form of a portion of a circle in the lower toothed wheel, an oblong slot in the form of a portion of a circle in the medial hinge plate, an oblong slot in the form of a portion of a circle in the lateral hinge plate, where the three oblong slots are congruent when the knee-joint orthesis is extended, and two sleeves which
   a) extend from the medial hinge plate into the oblong slot of the lateral hinge plate,
   b) can be fixed in their position in the oblong slot of the lateral hinge plate by means of screws, which are guided in the inside of the sleeves, and nuts, which are guided in the oblong slot of the medial hinge plate.

6. Knee-joint orthesis according to claim 1, wherein the thigh part and the lower leg part consist of a frame structure which is applied in particular in an anterior position on the leg.

7. Knee-joint orthesis according to claim 6, wherein the frame structure, of composite design, consists of a combination of a light metal frame, inner pads and an outer cover and wherein said frame structure is contourable to an individual's leg.

8. Knee-joint orthesis according to claim 1, wherein the leg and thigh parts are connected to the hinge parts through adjustable connections comprising oblong slots in each of said parts, the oblong slots in the leg and thigh parts being oriented 90° to the oblong slots in the hinges.

* * * * *

UNITED STATES PATENT AND TRADEMARK OFFICE
CERTIFICATE OF CORRECTION

PATENT NO. : 6,309,368 B1 Page 1 of 1
DATED : October 30, 2001
INVENTOR(S) : Herzberg et al.

It is certified that error appears in the above-identified patent and that said Letters Patent is hereby corrected as shown below:

Column 6,
Line 5, "wherein that the" should read -- wherein the --

Signed and Sealed this

Twenty-second Day of February, 2005

JON W. DUDAS
*Director of the United States Patent and Trademark Office*